US010161882B1

(12) United States Patent
Kaizerman et al.

(10) Patent No.: US 10,161,882 B1
(45) Date of Patent: Dec. 25, 2018

(54) METHOD OF EXAMINING LOCATIONS IN A WAFER WITH ADJUSTABLE NAVIGATION ACCURACY AND SYSTEM THEREOF

(71) Applicant: Applied Materials Israel Ltd., Rehovot (IL)

(72) Inventors: Idan Kaizerman, Meitar (IL); Mark Geshel, Kfar-Saba (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 0 days.

(21) Appl. No.: 15/222,824

(22) Filed: Jul. 28, 2016

(51) Int. Cl.
*G06F 17/00* (2006.01)
*G01N 21/95* (2006.01)
*G06F 17/50* (2006.01)

(52) U.S. Cl.
CPC ..... *G01N 21/9501* (2013.01); *G06F 17/5081* (2013.01)

(58) Field of Classification Search
USPC .......................................................... 716/52
See application file for complete search history.

(56) References Cited

U.S. PATENT DOCUMENTS

| 2002/0149050 | A1* | 10/2002 | Fazio ............... H01L 21/28512 257/314 |
| 2005/0234684 | A1* | 10/2005 | Sawicki .............. G06F 17/5045 703/1 |
| 2011/0209112 | A1* | 8/2011 | Laub ................... G06F 17/5068 716/132 |
| 2016/0085897 | A1* | 3/2016 | Jeong ................. G06F 17/5072 716/122 |

* cited by examiner

*Primary Examiner* — Mohammed Alam
(74) *Attorney, Agent, or Firm* — Lowenstein Sandler LLP

(57) ABSTRACT

A method, computerized system and computer program product for examining an object using a processor operatively connected to a memory, the method comprising: accommodating in the memory data indicative of a plurality of alignment targets, each alignment target associated with a target location on an object; accommodating in the memory a plurality of locations to be captured; and selecting by the processor an alignment target subset of the plurality of alignment targets, such that each of the plurality of locations is associated with and is within a determined distance from a single alignment target from the alignment target subset, the distance determined in accordance with a provided field of view, and wherein the alignment target subset comprises fewer targets than locations to be reviewed, the alignment target being usable for aligning the object relative to an examination tool for capturing the locations associated with the single alignment target.

20 Claims, 9 Drawing Sheets

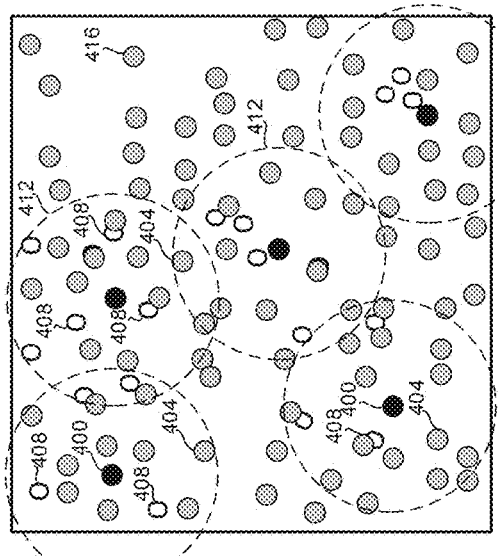
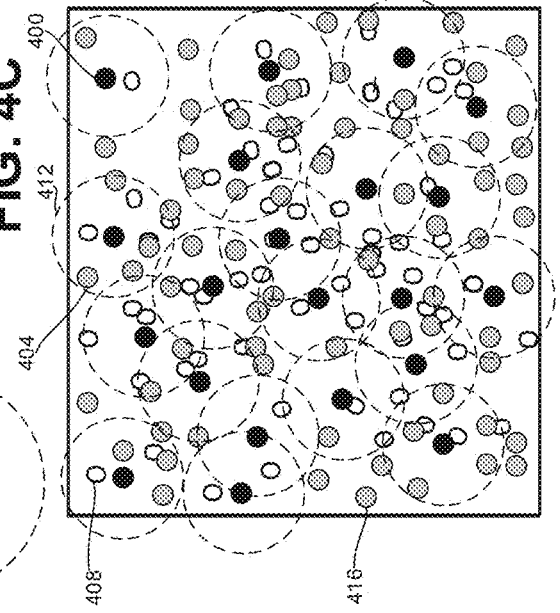
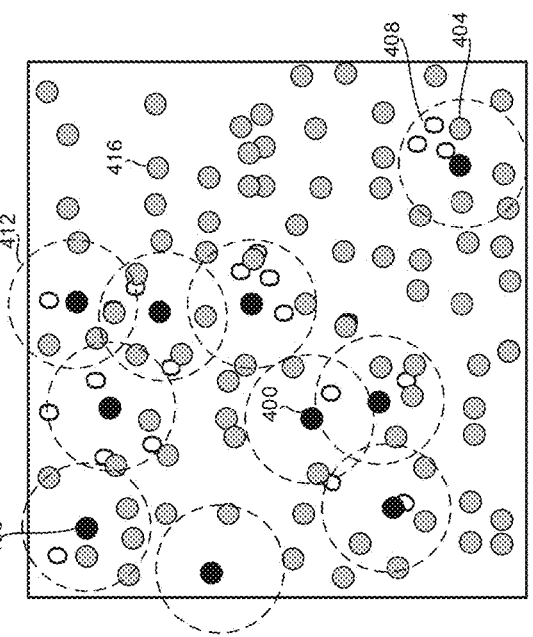
FIG. 4A
FIG. 4B
FIG. 4C

METHOD OF EXAMINING LOCATIONS IN A WAFER WITH ADJUSTABLE NAVIGATION ACCURACY AND SYSTEM THEREOF

TECHNICAL FIELD

The presently disclosed subject matter relates to location-based examination of objects such as semiconductor wafers, masks and the like, and more particularly to increasing the efficiency and accuracy of such examination.

BACKGROUND

Various objects such as semiconductor wafers, masks, printed circuit boards, solar panels and microelectromechanical devices are manufactured by manufacturing processes that are highly complex and costly, comprise multiple stages, and require very accurate machines.

Current demands for high density and performance associated with ultra large scale integration require formation of device features with high precision and uniformity. The usage of such device features necessitates automated process monitoring, including frequent and detailed examination of specimens during the manufacturing process.

The term "examination", unless specifically stated otherwise, used in this specification in relation to a wafer, should be expansively construed to cover any kind of examination, including but not limited to detection and/or classification of defects in an object (for example, semiconductor wafers) provided by using non-destructive inspection tools. By way of non-limiting example, examination can include generating one or more recipes for examination and/or parts thereof, runtime inspection (e.g. scanning in a single or in multiple scans), reviewing, and measuring and/or other operations provided with regard to the wafer or parts thereof using the same or different inspection tools. Such examination can be carried out by optical examination techniques, charged-particle examination techniques (such as electron beam and ion beam techniques), metrology tools, or any other known technique or tool.

In the context of examination by way of defect detection, in order to find defects, various examination steps can be integrated into the manufacturing process, including inspection and review. The examination steps can be performed a multiplicity of times, for example at certain stages such as after the manufacturing or processing of certain layers, or the like.

The term "defect" used in this specification should be expansively construed to cover any kind of abnormality in examination results or undesirable feature formed on or within a wafer. The term "defect" may relate to a location on a wafer that is identified as a location of a suspected defect, a location of interest representing a location to be further reviewed, and a location that is identified as a location of a redetected defect or a classified defect. A variety of non-destructive inspection tools includes, by way of non-limiting example, scanning electron microscopes, atomic force microscopes, optical inspection tools, metrology, etc. While in some contexts the defect location may refer to a single point, whether in two or three dimensional space, in other contexts the term may relate to a space containing a possible defect, such as a one, two or three dimensional area.

By way of non-limiting example, examination can employ a two phase "inspection and review" procedure.

The term "inspection" refers to scanning and analyzing a wafer or a part thereof, in order to detect locations in which defects may be found. Suspicious locations reported by inspection may include true defects, false positive reports, and nuisance defects, which are harmless.

The term "review" refers to capturing and analyzing one or more specific locations, for example locations of possible defects reported by the inspection process, locations of interest derived from design data, etc. In some embodiments, the term "review" may also refer to, mutatis mutandis, to performing metrology procedures.

Typically, inspection is performed at higher speed and lower resolution than review. Thus, inspection can be used for covering larger areas and detecting possible defects, wherein some or all of which may later be reviewed and examined.

In some embodiments, inspection and review can be performed by different tools, but in other embodiments they can be performed by the same tool.

The complex manufacturing process is not error-free and such errors may cause faults in manufactured objects. Such faults may include defects that can harm operation of the object, false positive findings, which may seem to contain a defect, but no actual defect exists at the area, and nuisances, which may be defects but do not cause any harm or malfunction of the manufactured unit. Errors may include linear or non-linear errors, such as mechanical, electrical or optical errors, in addition to faults in the raw material, human errors and others may cause defects in the wafers. Additional errors may be caused by spatio-temporal factors, such as temperature changes of the wafer, occurring after one or more captures, which may cause slight deformations of the wafer.

GENERAL DESCRIPTION

In accordance with certain aspects of the presently disclosed subject matter, there is provided a method of examining an object using a processor operatively connected to a memory, the method comprising: accommodating, in the memory, data indicative of a plurality of alignment targets, each alignment target associated with a target location on an object; accommodating, in the memory, a plurality of locations to be captured; and selecting, by the processor, an alignment target subset of the plurality of alignment targets, such that each of the plurality of locations is associated with and is within a determined distance from a single alignment target from the alignment target subset, the distance determined in accordance with a provided field of view, and wherein the alignment target subset comprises fewer targets than locations to be reviewed, the alignment target being usable for aligning the object relatively to an examination tool for capturing the locations associated with the single alignment target. The method can further comprise: for at least a first location of the plurality of locations: aligning the object such that a capture device can capture an alignment target associated with the first location; capturing by the examination tool a first image of the object including the alignment target; determining an actual location of the alignment target in the first image; determining a transformation between the actual location and the target location of the alignment target; moving the object such that an examination tool captures a transformed location obtained by applying the transformation to the first location; and capturing a second image of the object including the transformed location. The method can further comprise: once an object is received for examination: receiving a list comprising one or more proximate locations for points of interest on the object; determining a target having a location closest to one of the proximate locations; aligning the object relatively to the examination tool in accordance with the location; and capturing a part of the object including the point of interest. The method can further comprise: for at least a first location, and a second location associated with a different alignment target than the first location: determining a first reference location, a second reference location, corresponding, respectively, to the first location and the second location, and a second alignment target common to the first reference location and the second reference location, all located in one area which is different than areas of the first location and the second location. The method can further comprise: moving the object such that the examination tool captures the second target; capturing a third image of the object including the second target; determining an actual second reference target location within the third image; determining a reference transformation between the actual reference target location and the a location of the second target; moving the object such that the examination tool captures a first transformed reference location obtained by applying the reference transformation to the first reference location; and capturing a fourth image of a fourth part of the object including the first transformed reference location; moving the object such that the examination tool captures a second transformed reference location obtained by applying the reference transformation to the second reference location; and capturing a fifth image of a fifth part of the object including the second transformed reference location; and subject to detecting differences between areas of the second image associated with the first transformed location and of the fourth image associated with the first transformed reference location, indicating a defect in the object. The method can further comprise: for at least the first location, and a second location associated with the alignment target of the first location: determining a first reference location and a second reference location, corresponding, respectively, to the first location and the second location associated with a common alignment target, wherein the first reference location, the second reference location and the alignment target are located in one area which is different but at a maximal predetermined distance from areas of the first location and the second location. The method can further comprise: moving the object such that the examination tool captures a first transformed reference location obtained by applying the transformation to the first reference location; and capturing a third image of a third part of the object including the first transformed reference location; moving the object such that the examination tool captures a second transformed reference location obtained by applying the reference transformation to the second reference location; and capturing a fourth image of a fourth part of the object including the second transformed reference location; and subject to detecting differences between areas of the first image and the third image associated with the first location, indicating a defect in the object. Within the method, transformation is optionally a two dimensional transformation. The method can further comprise: receiving one or more review locations or one or more regions of interest from a human user. Within the method, the target subset is optionally selected using clustering. Within the method, the target location and first location are optionally indicated in coordinates associated with design data of the object. The method can further comprise: receiving design data of the object; rasterizing a synthetic image of the object, based on the design data; and determining the plurality of targets locations by applying image processing techniques to the synthetic image. The method can further comprise: receiving some of the design data for one or more potential target locations; and determining exact target location by applying processing techniques to the design data. Within the method the plurality of targets are determined in accordance with uniqueness in an area surrounding each target, or such that an area surrounding each target comprises a multiplicity of edges in at least two directions. The method can further comprise validating the target locations against an image of the object. Within the method, the plurality of targets optionally include a primary target and a secondary target for each region of the object. Within the method, each of the plurality of locations is optionally associated with a single alignment target. Within the method, the examination tool is optionally an optical inspection device or a charged particle beam based examination tool.

In accordance with other aspects of the presently disclosed subject matter, there is provided a computerized system for examining an object, the system comprising a processor configured to: accommodate in the memory data indicative of a plurality of targets, each target associated with a target location; accommodate in the memory a plurality of review locations to be captured; and select by the processor an alignment target subset of the plurality of targets, such that each of the plurality of locations is associated with and is within a determined distance from a single alignment target from the target subset, the distance determined in accordance with a provided field of view, and wherein the alignment target subset comprises fewer targets than locations in the review locations, the alignment target being usable for aligning the object relative to an examination tool for capturing the locations associated with the single alignment target.

In accordance with other aspects of the presently disclosed subject matter, there is provided a computer program product comprising a computer readable storage medium retaining program instructions, which program instructions, when read by a processor, cause the processor to perform a method comprising: accommodate in the memory data indicative of a plurality of targets, each target associated with a target location on an object; accommodate in the memory a plurality of locations to be captured; and select by the processor an alignment target subset of the plurality of targets, such that each of the plurality of review locations is associated with and is within a determined distance from a single alignment target from the target subset, the distance determined in accordance with a required accuracy, and wherein the alignment target subset comprises fewer targets than locations to be reviewed, the alignment target being usable for aligning the object relative to an examination tool for capturing the locations associated with the single alignment target.

BRIEF DESCRIPTION OF THE DRAWINGS

In order to understand the present disclosure and to see how it can be carried out in practice, embodiments will be described, by way of non-limiting examples, with reference to the accompanying drawings, in which:

FIGS. 4A, 4B and 4C show schematic illustrations of exemplary clustering options for review locations and targets on a wafer die, in accordance with some exemplary embodiments of the disclosure;

DETAILED DESCRIPTION

Figure 1A:
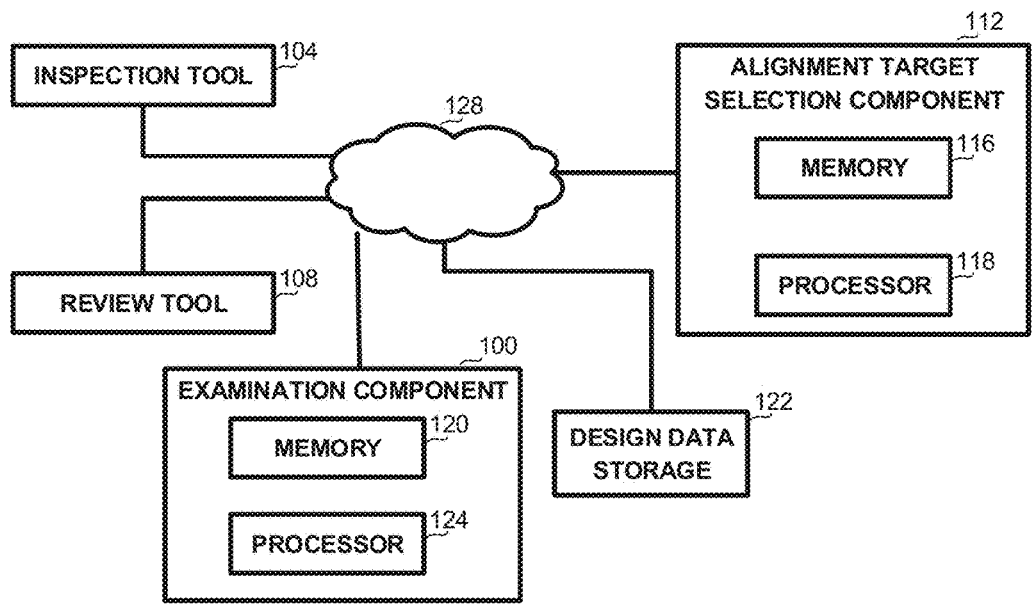
FIG. 1A is a generalized block diagram of a computerized environment for examining a wafer in accordance with some exemplary embodiments of the disclosure.

For simplicity, aspects of the disclosure will be described with reference to examination of semiconductor wafers. The disclosure is not limited to examination of wafers and is applicable to location-based examination of other objects such as lithographic masks and reticles, printed circuit boards, solar panels, microelectromechanical devices and other objects.

In the following detailed description, numerous specific details are set forth in order to provide a thorough understanding of the disclosure. However, it will be understood by those skilled in the art that the presently disclosed subject matter can be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "processing", "computing", "representing", "comparing", "generating", "assessing", "matching", "updating" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities.

The operations in accordance with the teachings herein can be performed by a computer specially constructed for the desired purposes or by a general-purpose computer specially configured for the desired purpose by a computer program stored in a non-transitory computer-readable storage medium.

The terms "non-transitory memory" and "non-transitory storage medium" are used herein should be expansively construed to cover any include any volatile or non-volatile computer memory suitable to the presently disclosed subject matter.

The term "design data" used in the specification should be expansively construed to cover any data indicative of hierarchical physical design (layout) of a specimen. Design data can be provided by a respective designer and/or can be derived from the physical design (e.g. through complex simulation, simple geometric and Boolean operations, etc.). Design data can be provided in different formats as, by way of non-limiting examples, GDSII format, OASIS format, etc. Design data can be presented in vector format, grayscale intensity image format or otherwise. Design data may comprise design structural elements that represent different features to be formed on one or more layers of a specimen. As known in the contemporary art, a design structural element can be constructed as a geometrical shape with a closed contour or a geometrical shape combined with insertion of other structural elements. By way of non-limiting examples, a given design structural element can comprise one or more STRUCTURE elements inserted by means of SREF, AREF directives in GDSII format, or can comprise one or more CELL elements inserted by means of PLACEMENT and REPETITION (OASIS format).

The term "review location" or "location" used herein should be expansively construed to cover any location on a wafer required to be reviewed. A location may relate to a point, expressed as a set of coordinates in two or three dimensions, or to a line or two- or three-dimensional area, depending on the context. Review locations may be associated with revealed or potential defects, patterns of interest (e.g., crossing of specific design elements), or otherwise defined regions of interest determined during one or more examination stages. For example locations may be detected during inspection, by taking one or more optical images of the wafer or part thereof, and comparing an obtained image or features therein to an expected image, to predetermined features from design data, or to an image of another die, which may be more or less adjacent, wherein the differences may be regarded as potential defects. The review locations may further include any other locations it may be required to review, which may be provided automatically, manually, or the like, provided by a user, or the like. Review location can be specified in design coordinates and/or coordinates tied to a wafer, die, or a region thereof. It is noted that the review locations can be a subset selected for review among a larger group of review locations of interest.

The term "alignment target" or "target" used herein should be expansively construed to cover any wafer area recognizable within its environment. For example, a recognizable image of a target can be characterized by distinct features such as a pattern unique in its environment, a multiplicity of edges in two or more dimensions, or the like. Each target is associated with a target location, expressed for example as two coordinates in a predetermined coordinate system (e.g. design coordinates and/or coordinates tied to a wafer, die, or parts thereof). Targets can be useful in navigating to and capturing one or more review locations.

The term "reference location" should be expansively construed to cover a location corresponding to another location specified in a set of coordinates tied to a certain point or area of the wafer. For example, when a wafer comprises a multiplicity of allegedly identical dies, a location having a set of coordinates relative to one die may be associated with one or more reference locations located at the same set of coordinates relative to another die.

Reference is now made to FIG. 1A, showing a computerized environment for examining a wafer, according to some embodiments of the disclosure.

FIG. 1A illustrates examination component 100, inspection tool 104, review tool 108, alignment target selection component 112, and design data storage 122.

A network 128 is coupled to examination component 100, inspection tool 104, review tool 108, alignment target selection component 112, and design data storage 122. For example, network 128 may be a fab communication system. For simplicity of explanation, only a single inspection tool 104 and a single review tool 108 are shown. It should be noted that in practice, a plurality of inspection tools and a plurality of review tools can be connected via network 128. For further simplicity of explanation, a single alignment target selection component 112 and a single examination component 100 are shown. It should be noted, however, that more than one alignment target selection component 112 or more than one single examination component 100 can be used. Additionally or alternatively, each of alignment target selection component 112 and examination component 100 can be implemented as one or more interconnected computing platforms.

The disclosure is not limited by the type of physical communication and coupling provided between the various entities of FIG. 1A. Any two components may be connected directly, via network 128, via any other component, whether such component is shown or not in FIG. 1A.

Although for simplifying the explanation alignment target selection component 112 and examination component 100 are shown as stand-alone computer systems, it is noted that any of them can be a part of inspection tool 104 or of review tool 108. Alternatively, alignment target selection component 112 and examination component 100 can be implemented as one computer system. According to some embodiments of the disclosure, one or more of alignment target selection component 112 and examination component 100 can be facilitated as a hardware utility which is placed on an electronic rack of, for example, inspection tool 104, review tool 108 or any other computing system associated with the fab.

Examination component 100 can be configured to execute the methods of FIG. 1B (including activating alignment target selection component 112), 6 and 7 below, and alignment target selection component 112 can be configured to execute step 150 of FIG. 1B below.

Alignment target selection component 112 can include a memory unit 116 and a processor 118.

Figure 2:
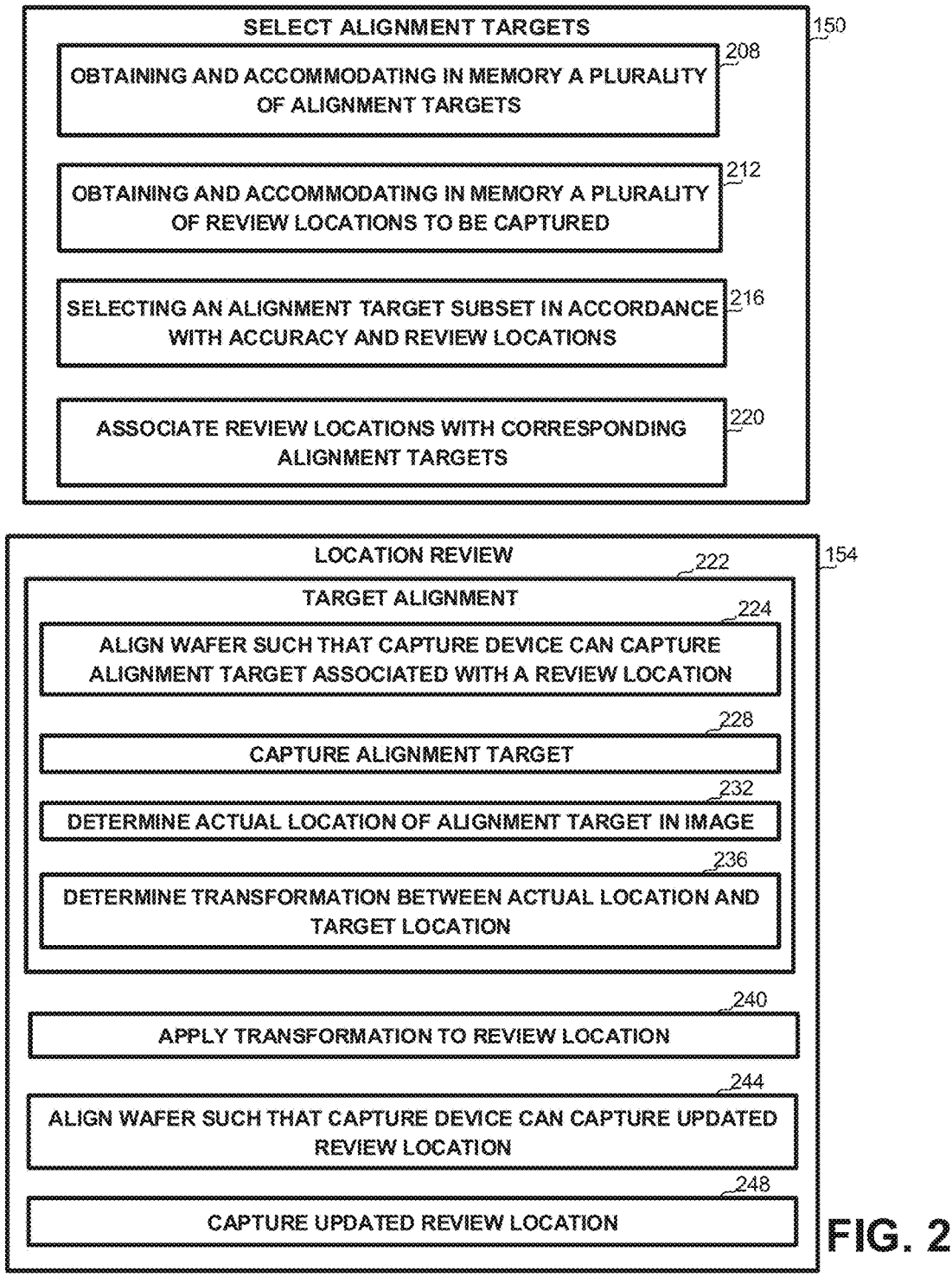
FIG. 2 illustrates a generalized flowchart of examining a wafer in accordance with some exemplary embodiments of the disclosure.

Memory unit 116 can be configured to store at least one of: information required for executing a method such as depicted in step 150 and detailed in FIG. 2, and software required for executing any of said method, or information generated during the execution of said method.

Processor 118 can be configured to perform any operation required during any step of one or more of the method such as depicted in step 150 and detailed in FIG. 2.

Examination component 100 can include a memory unit 120 and a processor 124.

Figure 1B:
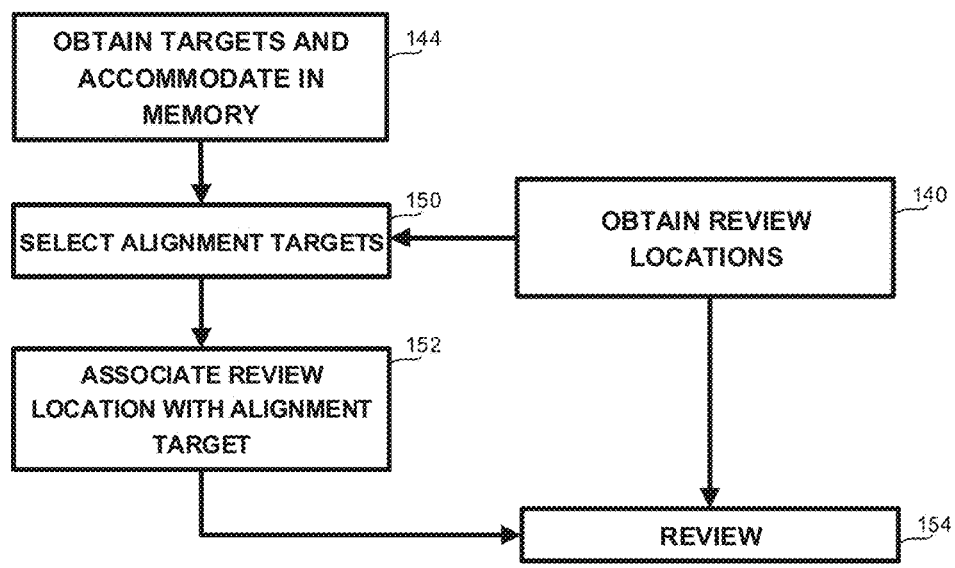
FIG. 1B illustrates a generalized flowchart of an examination process of a wafer, in accordance with some exemplary embodiments of the disclosure.
Figure 6:
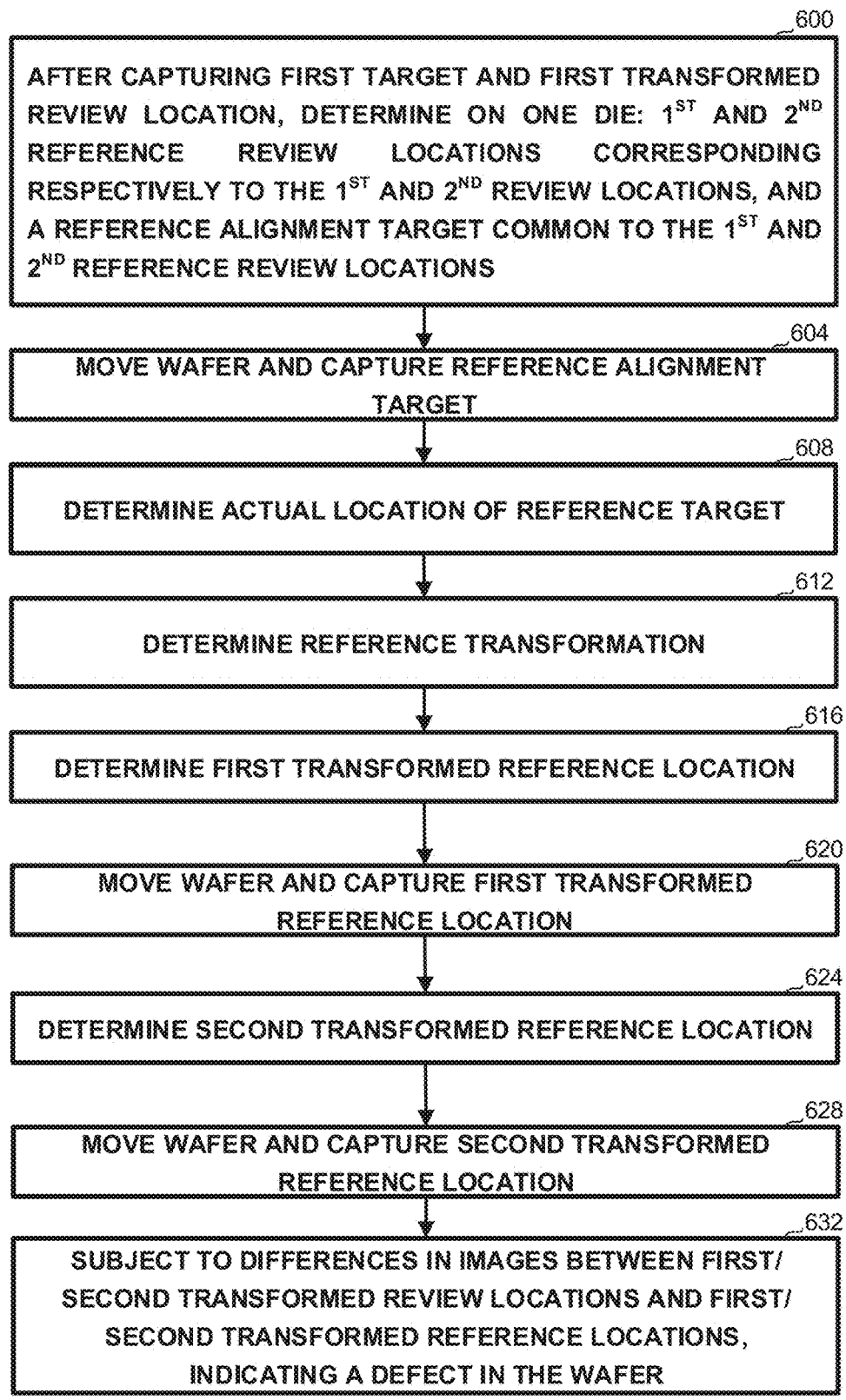
FIG. 6 shows a generalized flowchart of using alignment targets when performing detection by means of die to die comparison corresponding to FIG. 5C, in accordance with some embodiments of the disclosure.
Figure 7:
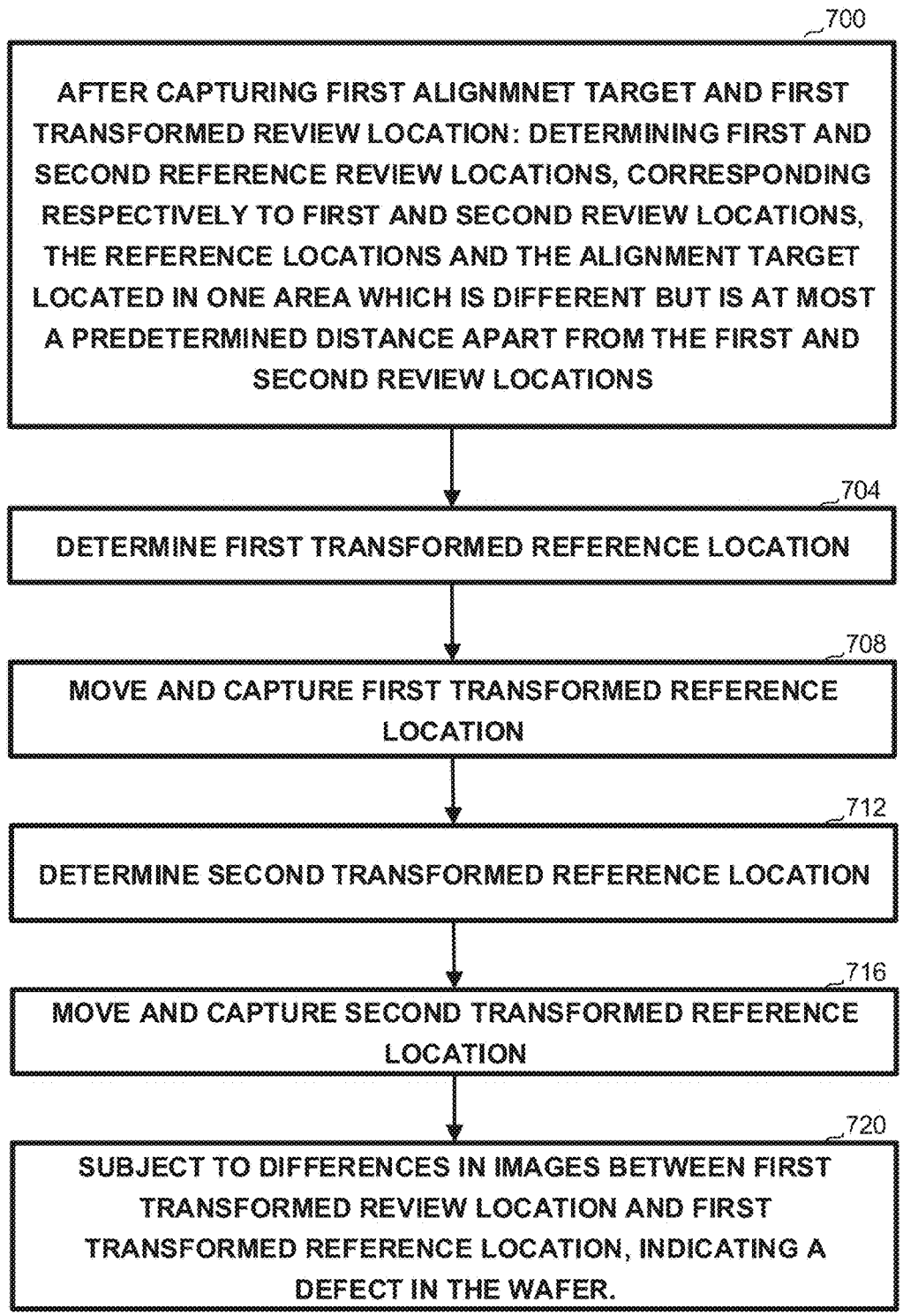
FIG. 7 shows a generalized flowchart of using alignment targets when performing detection by means of die to die comparison corresponding to FIG. 5D, in accordance with some exemplary embodiments of the disclosure.

Memory unit 120 can be configured to store at least one of: information required for executing one or more of the methods depicted in FIGS. 1B, 6 and 7, and software required for executing any of said methods, or information generated during the execution of said methods.

Processor 124 can be configured to perform any operation required during any step of one or more of the methods depicted in FIGS. 1B, 6 and 7. Referring now to FIG. 1B, this shows a generalized flowchart of examining a wafer, in accordance with some exemplary embodiments of the disclosure. The flowchart is described in association with the elements of FIG. 1A described above.

It will be appreciated that the examination process can repeat multiple times, for different layers, or different parts of the wafer, different stages on the manufacturing process, or the like.

Examination component 100 detailed below can be configured to obtain review locations (140).

As illustrated in FIG. 1B, examination component 100 can be configured to obtain a multiplicity of targets (144) provided by a user, determined automatically, or the like. Each target may be associated with a target location indicating its coordinates, for example its top left corner, if applicable. Each target may be square, rectangular, cyclic, or may have any other shape. The targets may be obtained, for example, by calculations that use design data stored in design data storage 122 which may also be implemented as a memory device collocated with memory 116, memory 120 or separately.

Examination component 100 can be configured to activate alignment target selection component 112 for selecting (150), out of the received targets, targets usable for navigating to review locations and unique within their surrounding area, such targets being referred to hereinafter as "alignment targets". The alignment targets can be accommodated in memory.

As will be further detailed with reference to FIGS. 3, 4A-4C and 5A-5D below, the alignment targets are used during navigation. The review tool can apply a navigation process for navigating to a possible defect in order to capture the possible defect and its environment, and then navigate to further ones and capture them as well.

Navigation to a location may be widely construed to cover moving the wafer within or relative to the review tool, such that the review tool may perform an action, such as capture an image of the review location. Alternatively, and depending on the review tool, one or more members of the review tool may be moved relative to the wafer.

However, the navigation process may suffer from navigation errors that may cause the review tool to capture a wrong location when reviewing a suspected defect. Such navigation errors may stem from a number of causes. Errors may relate to inaccuracies in the locations as received from the inspection tool, to mechanical inaccuracies preventing accurate navigation, to inaccuracies in translations between the various coordinate systems used, including for example the design data coordinate system, the inspection coordinate system and the review coordinate system, or others. Errors may also be caused by spatio-temporal factors, such as temperature changes of the wafer occurring after one or more possible defects have been captured, which may cause slight deformations of the wafer. Further errors may be subject to ambiguity in identifying the wafer elements captured at the location. It will be appreciated that further errors may occur due to other reasons.

Some exemplary embodiments of the disclosure provide a method for reducing navigation errors of an examination tool in examining an object, to thereby ensure that the navigation error when examining an object at one or more locations at a given field of view shall not exceed the given field of view.

In accordance with certain embodiments of the presently disclosed subject matter, in order to overcome the navigation errors and capture the required review locations, alignment targets can be used. The alignment targets can be specified in a coordinate system which may be known at all examination stages, for example the coordinate system available during the design of the wafer, e.g., the Computer Aided Design (CAD) data coordinate system, which is also available during the inspection and review stages.

The navigation process is characterized by a required accuracy value, typically provided by a user, or determined upon a field of view given for a certain examination device. The accuracy value indicates the maximal radius for which the navigation error is smaller than the field of view and is therefore acceptable. Thus, the accuracy may be described as the maximal distance between a designated location to which it is required to navigate the wafer relatively to the review tool, and the location to which the wafer has been navigated. For example, if the designated coordinates of an object are [100, 100], then if the accuracy is 1 micron, then the object is guaranteed to be within a circle bound by x=99, x=101, y=99 and y=101 (all in microns). Thus, a field of view bound by a square of at least 2 micron*2 micron centered around coordinates [100,100] ensures that the object is present within the captured image. The alignment target shall be selected to enable it unambiguous identification within the field of view.

As technology progresses, the pixels grabbed by the imaging devices need to and indeed get smaller, therefore more pixels are required for covering the same area, thus increasing the image acquisition time, and also limiting the number or locations it is practical to review. The time increase and number of locations limitation is particularly true when capturing with a scanning electron microscope.

If the navigation errors are high, then in order for each of the review locations to be within the required accuracy from one of the targets, it may be required to select more targets wherein each target is used for navigating to fewer review locations, which will increase the overall review time.

Thus, the accuracy may be selected as the maximal distance between a target and a review location for which the navigation error is below the field of view.

Figure 3A:
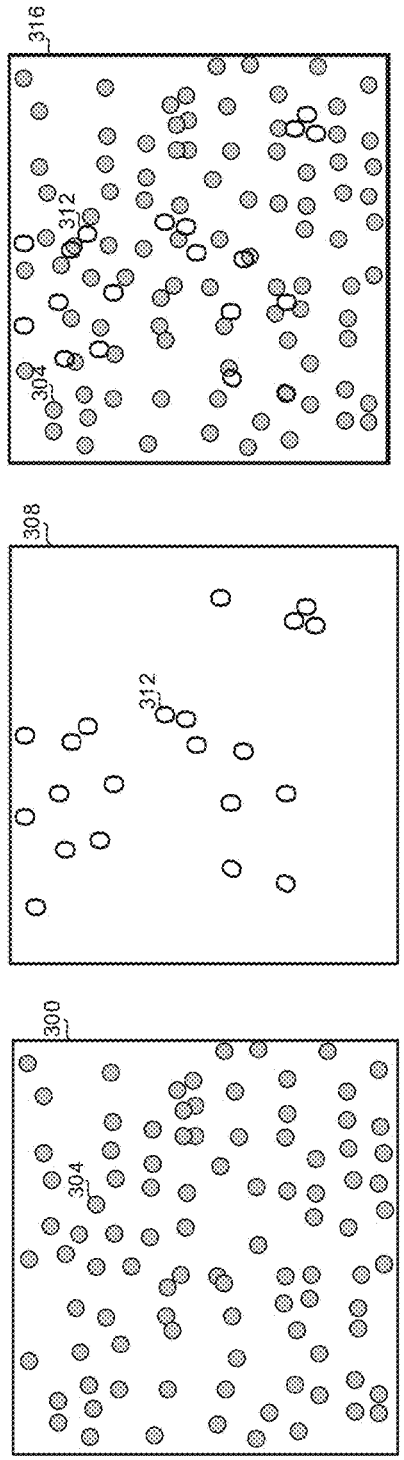
FIG. 3A shows an exemplary illustration of targets and review locations on a wafer die, in accordance with some exemplary embodiments of the disclosure.
Figure 3B:
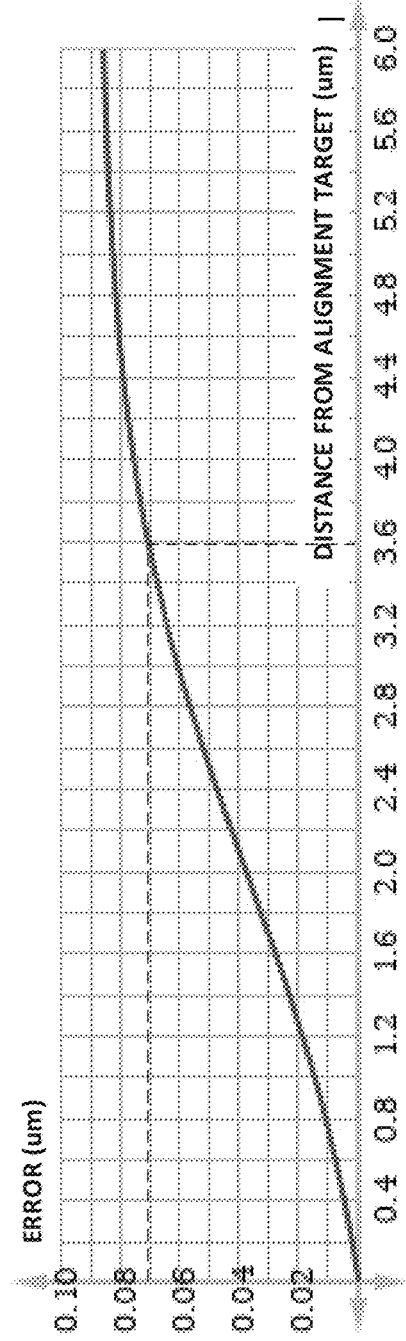
FIG. 3B shows an exemplary graph for a particular examination device, upon which the accuracy parameter is determined.

Reference is now made to FIG. 3B, showing an exemplary graph of the relationship between the navigation error when navigating from a target to a location and the distance between the location and the target, for a particular device. In view of the graph, the maximal distance from an alignment target may be selected to ensure navigation error is still smaller than the desired field of view radius. The desired field of view is derived from the grab time and pixel size and defines the number of locations which can be reviewed in a given period of time, for example within an hour. For example, if the desired field of view has a radius of 0.07 um, then an alignment target should be found in a radius smaller than 3.6 um from the review location. Navigating from alignment target with a distance smaller than 3.6 um from the review location guarantees that the review location will be found within the 0.07 um radius.

It will be appreciated that large navigation errors imply a requirement for grabbing an area of larger radius around the target. For a given number of pixels per captured image, the implication is lower resolution. Increasing the resolution, however, will consume more time and may thus limit the number of reviewed locations.

Navigation errors are becoming a more challenging aspect as the design rule of the printed circuit patterns, for example 20 nanometer, 10 nanometer, and so on, keeps getting smaller.

Therefore, in accordance with certain embodiments of the currently presented subject matter, in order to review more locations at higher accuracy, an approach of local alignment can be used.

It will be appreciated that a tradeoff exists between the speed and accuracy of the review process. Using more alignment targets provides for higher accuracy and higher time requirements due to a larger number of full navigation processes being required, while using fewer alignment targets provides for lower accuracy and lower time requirements.

Typically, a few alignment targets are indicated for a wafer, such as between 5 and 20. However, a large distance between a target and a location to be reviewed may introduce further deviations and errors. Thus, multiple targets can be defined for each wafer, for example over a grid. Each location can then be navigated to by using a nearby target. However, the navigation to the target associated with each location is lengthy, since full alignment is required for each review location. In order to reduce the review time, a subset of the targets, to be used as alignment targets can be selected, such that each alignment target is used for navigating to a multiplicity of review locations, thus significantly reducing the navigation time and enabling the review of more review locations.

Thus, at step 150, a subset of the targets can be selected as alignment targets in accordance with the review locations to be reviewed and the accuracy, to provide for navigation and capturing of the review locations with enhanced accuracy and efficiency.

The subset of the alignment targets can be selected such that each review location is associated with and at a distance not exceeding a threshold from one of the alignment targets. Selecting an alignment target per each review location can enable accurate navigation, but may introduce the same spatio-temporal errors, causing a long review process, since a separate alignment is required per each review location. Thus it can be attempted to reduce the number of the alignment targets such that for at least one alignment target, a multiplicity of review locations are associated with the alignment target, and at a distance of at most the predetermined threshold therefrom. Thus, with one alignment operation it can be possible to navigate to the area of a multiplicity of review locations, such that after an initial navigation to the alignment target, only a short additional move is required for navigating to each of the review locations associated with the alignment target.

Examination component 100 can be configured to associate (152) each review location with an alignment target, for example the alignment target that is closest to the location, the alignment target associated with a cluster to which the review location is assigned as detailed below, etc.

Examination component 100 can be configured to activate review (154) of the review locations. As further detailed below, reviewing can be performed by navigating to one or more of the review locations. In accordance with certain embodiments of the presently disclosed subject matter, in order to navigate to a review location, the review tool can first navigate to an alignment target close to the required review location, capture a wafer area comprising the alignment target and identify the alignment target within the captured image. The review tool can then determine the transformation between the expected location and the actual location, apply the transformation to the associated review location, and navigate to the review location in accordance with the coordinates corrected by the applied transformation. The enabled relative proximity between the review location and the alignment target ensures that the transformation obtained for the alignment target is also applicable to the review location, such that the review location will indeed be captured in accordance with the required accuracy Referring now to FIG. 2, showing a generalized flowchart of steps in a method for reviewing a wafer, in accordance with some exemplary embodiments of the disclosure.

Alignment target selection component 112 can be configured to perform alignment target selection (150) from the available targets once the review locations to be reviewed are available. Examination component 100 can activate review location review (154) performed for reviewing the wafer at the review locations.

Alignment target selection step 150 can include step 208 for obtaining and accommodating in memory a plurality of targets. The targets can be received from a storage device, from a user, from a third party or any other external source. Alternatively, the targets can be determined.

In some embodiments determining the targets can be based on the design data of the wafer. In some embodiments, a synthetic image of the wafer can be created, for example rasterized, based on the design data, while taking into account physical properties of the wafer layers, including color, thickness, opacity properties, components or the like.

The targets should have features that make them easily recognizable in their environment. For example, they may be unique in their environment, can comprise a multiplicity of edges in one or two dimensions, possibly with a special arrangement, or the like.

Thus, once the synthetic image is available, certain areas can be indicated as being proper targets, by applying image processing techniques including but not limited to detection of edges, corners, blobs, points of interest, regions of interest, ridges, or the like. The detection may use any one or more techniques such as but not limited to histogram of gradients, binary descriptors, deep learning techniques, entropy based identification, feature detection, or the like.

Additionally or alternatively, a smaller part of the design data can be received for one or more of the potential target locations; and the exact target location of each such target can be determined by applying techniques such as polygon processing techniques to the design data. Polygon processing may include segmenting the polygons into lines and corners, thus dividing the potential target area to a grid of smaller regions. The uniqueness and matching scores may be calculated for each smaller region. The uniqueness score may be based on the similarity of a polygon to its adjacent polygons. The matching score may be based on the number of corners and line directions of a polygon. The smaller regions in the potential location may then be sorted by a combination such as a linear combination of uniqueness and matching scores: score=a*uniqueness score+b*matching score.

In some embodiments, the targets can be validated once a wafer is manufactured. For example, the targets as determined using the synthetic image can be compared against how the relevant area really appears, for example by comparing to an actual image of the wafer. If a possible target does not comply with the criteria, for example if the edges appear obscured for enabling proper registration, it can be deleted from the target collection.

Since it is not known a-priori where the review locations to be reviewed will be located, and thus which alignment targets can be used, it will be appreciated that having targets at high density and at substantially uniform distribution over the wafer, for example substantially along the lines of a two dimensional grid, can be useful for enabling proper selection of the alignment targets.

Alignment target selection component 112 can be configured to perform step 212, in which a plurality of review locations to be reviewed can be obtained and accommodated in memory. The review locations can comprise locations from a larger collection of review locations reported as possible defects by an inspection process. The review locations can further comprise regions of interest other than those reported by the inspection process.

Alignment target selection component 112 can be configured to perform step 216 in which a subset of the targets obtained on step 208 can be selected as alignment targets, in accordance with a received field of view parameter and with the review locations to be reviewed. The alignment targets can be selected such that each review location is at most at a predetermined distance from one of the alignment targets comprised in the subset.

It will be appreciated that the number of alignment targets selected may be determined in accordance with considerations associated with time, cost or navigation accuracy, as detailed above.

Alignment target selection component 112 can be configured to perform step 220, in which an alignment target that meets these conditions is determined for each review location. In some embodiments, the selected review locations can be clustered, for example using a mean shift clustering algorithm or K-means clustering algorithm with a kernel, or others. Thus each cluster is associated with one of the received targets, and all review locations in a cluster are at most at a predetermined distance from the target. Having a sufficient number and high density of targets enables clustering with such conditions. The collection of all the targets associated with the clusters makes the alignment targets.

The distance may also be regarded as a radius of a circle around the alignment target in which all review locations of the cluster are positioned. Thus, the distance can be selected such that the maximal error accumulated when the wafer is moved relative to the review tool from the alignment target to any of the review locations still maintains the review location within the field of view, and no further correction is required. For example, the distance can be determined in accordance with a formula or a look up table that associates distances on the wafer with accumulated navigation error. In one example, a distance of 1 mm between objects may imply an error of 100 nanometers, a distance of 2 mm may imply an error of 250 nanometers, or the like. Thus, the distance between each review location in a cluster and the alignment target associated with the cluster should not exceed a value whose associated error exceeds an error acceptable to a user.

The alignment targets can be stored, for example by storing the location, and optionally an image or another visual description of each alignment target.

Additionally or alternatively, a coverage area may be associated with each selected alignment target, wherein the size of each coverage area may be responsive to the desired accuracy of the navigation process and to the expected navigation errors. It will be appreciated that steps 216 and 220 can be performed together as one process, separately, with step 220 being performed as part of step 216, or the like.

Once the alignment targets are selected, a global or coarse alignment procedure using up to a predetermined number, for example up to 12 targets on the entire wafer, may ensure that the alignment target itself can be reached and found within a reasonable field of view. Then each review location can be captured and reviewed at step 154.

Examination component 100 can perform review location reviewing step 154 which can comprise target alignment steps 222, that can be performed once per cluster, such that when capturing two or more review locations associated with one cluster, steps 222 need not be repeated.

When performing target alignment steps 222, examination component 100 can perform or initiate alignment step 224 in which the wafer is aligned with the review capture device, such that the alignment target associated with the review location which is thus within the distance from the review location, can be captured by the review capture device, such as the SEM.

Examination component 100 can perform or initiate alignment target capturing step 228, in which the alignment target is captured. Since the field of view of the capture device is consistent with the navigation accuracy, the alignment target is known to be within the captured image.

Examination component 100 can be configured to perform or initiate step 232, in which the alignment target can be searched for in the captured image. Searching can comprise locating the image or visual characteristics of the alignment target within the captured image, optionally using image analysis techniques, for example as described in US Patent Application No. 2016-0035076 which is incorporated herein, or by any other known technique. The actual location of the alignment target can then be determined from its location within the captured image.

Examination component 100 can be configured to perform or initiate step 236, in which a transformation between the actual location of the alignment target and the location of the alignment target as determined can be performed. For example, the transformation can be expressed as a 3*3 transformation matrix (when the alignment target is two dimensional). Alternatively, the transformation can be expressed as a two dimensional vector. The transformation can represent the deviation of the alignment target from its intended location to the actual location, due to the navigation error or any other types of errors.

Once the transformation is available, then one or more of the review locations comprised in the cluster of review locations associated with the specific alignment can be captured.

Examination component 100 can be configured to perform or initiate step 240, in which the transformation determined at step 236 can be applied to a review location, to obtain a transformed review location. Due to the relatively small distance between the review location and the corresponding alignment target, the transformation can be relevant and correct, such that the required review location is indeed at the transformed location.

Examination component 100 can be configured to perform or initiate step 244, in which the wafer can be aligned with the capture device associated with the review tool, such that the transformed review location can be captured by the capture device associated with the review tool, such as the SEM.

Examination component 100 can be configured to perform or initiate step 248, in which the transformed review location can be captured, and the image can be reviewed.

Referring now to FIGS. 3, 4A, 4B and 4C showing exemplary illustrations of alignment target subset selection.

FIG. 3 shows an exemplary illustration of targets and review locations in a die.

Pane 300 of FIG. 3 shows a multiplicity of alignment targets 304 on die 300.

Pane 308 comprises a multiplicity of review locations 312 on a die, such as possible defect locations, regions of interest, or the like and pane 316 shows review locations 312 and targets 304 together.

It will be appreciated that it is required to select a smaller number of targets as alignment targets, such that substantially each review location is within a predetermined distance from one of the alignment targets. This requirement may be depicted graphically as each review location is within a circle of at most a predetermined radius, and whose center is located on one of the alignment targets. The radius of the circle represents the clustering distance.

FIGS. 4A, 4B and 4C show three clustering options for review locations 408 and alignment targets 400. In each option, a number of review locations are in at most a predetermined distance from an alignment target 400. Further possible targets 404 are not selected as alignment targets and are not used during review.

During review, an alignment target 400 can be navigated to, captured, and detected within the image, and a transformation can be determined between the designated location of alignment target 400 and the actual one. Review locations 408 within a circle whose center is the alignment target, can then be navigated to and captured, one by one. Once all review locations 408 have been captured, the next alignment target 400 and associated review locations 408 can be handled in the same manner.

FIG. 4A, in which fewer alignment targets are used, provides for fewer alignment operations and therefore faster review and better throughput. However, since the radius of bounding circle 412 is larger than the radius of the bounding circles shown in FIGS. 4B and 4C, some review locations and in particular the ones farther from the associated alignment target 400 may deviate from the transformed location, and their capturing may thus be inaccurate. If review locations are not captured, a larger field of view may be used for the examination, which implies a larger number of pixels and thus time. Alternatively, more alignment operations may be required, thus also increasing the examination time.

Reference is now made to FIGS. 5A, 5B, 5C and 5D showing exemplary schematic illustrations of methods for using alignment targets when detecting defects by comparing corresponding locations on adjacent dies in a wafer, in accordance with some embodiments of the disclosure.

It will be appreciated that although the squares formed by the grids in FIGS. 5A, 5B, 5C and 5D are sometimes referred to as dies of a wafer, wafers and dies constitute a non-limiting example and the figures and description may represent any other areas of an examined object.

When reviewing a review location suspected of being a defect, it can be required to capture the review location, as well as a reference location in a nearby area. For example, in addition to capturing the review location, which can be situated within a first die, a reference location in a second die, which can be a neighbor of the first die, can also be captured. The captured areas of the review location and the reference location can be compared, and if differences are spotted then it can be assumed that the review location indeed represents a defect or a nuisance, but is not a false alarm.

Figure 5A:
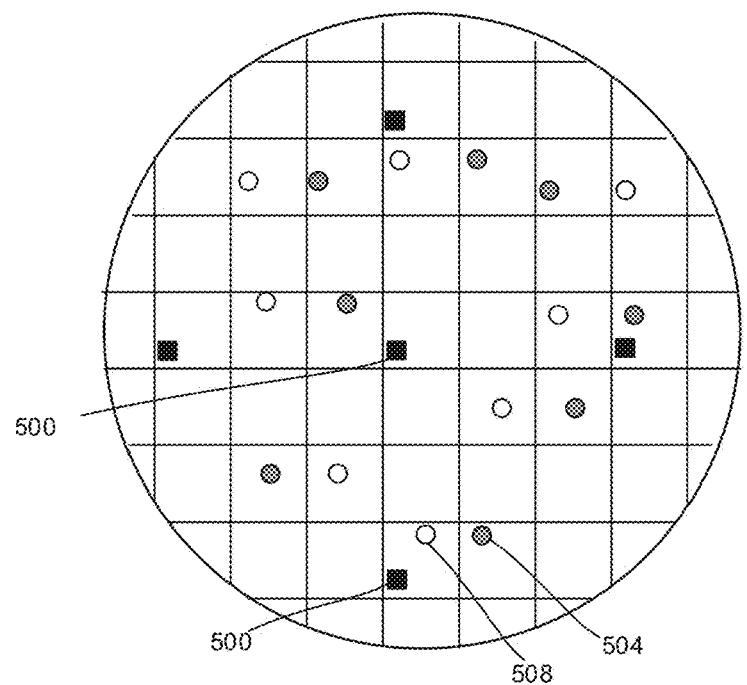
FIGS. 5A, 5B, 5C and 5D show exemplary schematic illustrations of methods for using alignment targets when performing detection by means of die to die comparison, in accordance with some exemplary embodiments of the disclosure.

FIG. 5A represents a global or coarse alignment case and shows a situation in which a small number, such as five, alignment targets 500 are spread over a wafer. In this case all alignment targets are captured, and compared against the image or features found at their expected locations on the wafer, in order to produce a two-dimensional offset vector which may be global for the whole wafer. Each review location 508 can then be captured, as well as a corresponding reference location 504 in a neighboring or another close die. Due to the small number of alignment targets, the deviation of each review location and each reference location from the intended coordinates may be large, thus leading to inaccuracies and possible misses in capturing the reported locations.

Figure 5B:
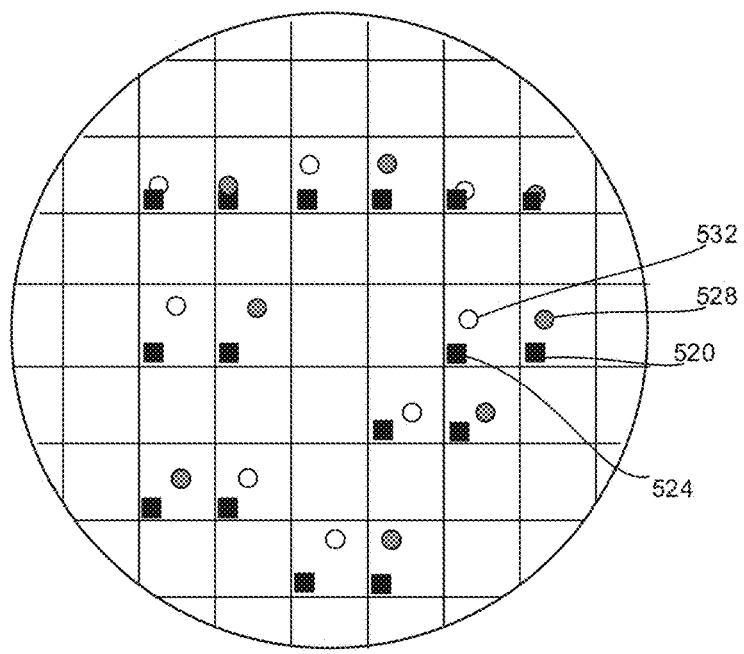

In the situation depicted in FIG. 5B, local alignment is applied, in which an alignment target 524 is associated with each review location 532, and a second alignment target 520 is associated with each reference location 528. Thus, the capturing of every review location 532 and every reference location 528 requires a separate alignment, which increases accuracy, but the review process takes time which is longer than in the situation of FIG. 5A.

Figure 5C:
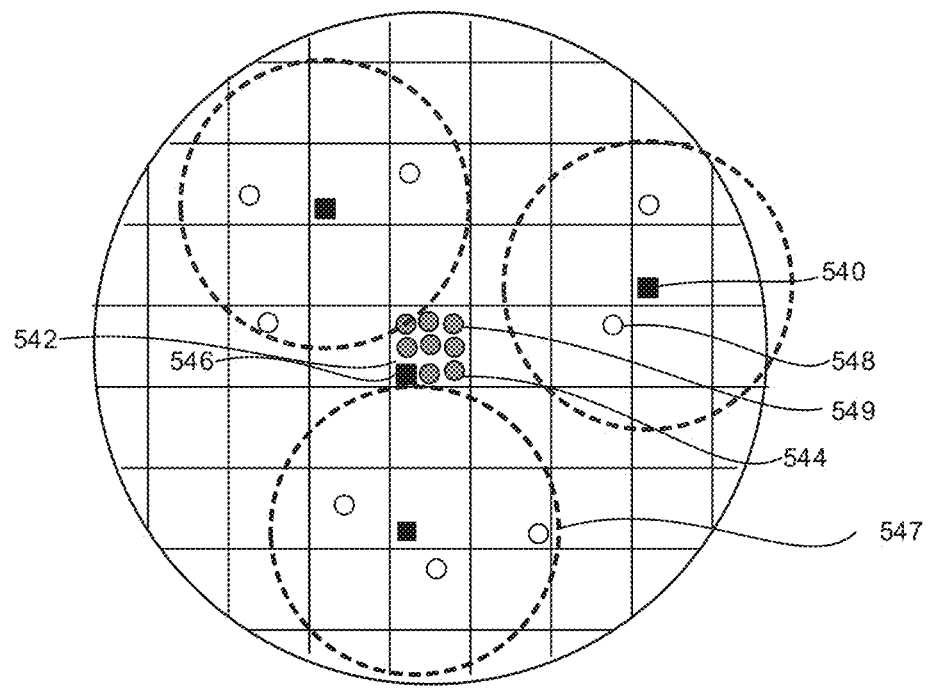
Figure 5D:
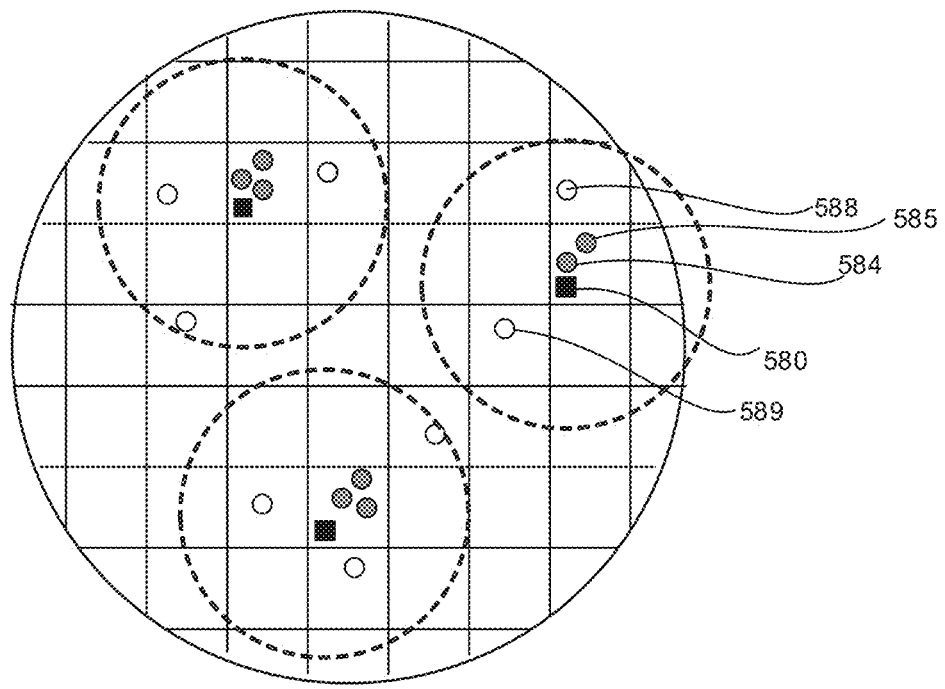

FIGS. 5C and 5D represent situations in which the alignment targets are selected dynamically based on the review locations which it is required to review.

FIG. 5C depicts a situation in which review locations 548 are clustered, wherein each cluster is associated with a target 540. In addition, all reference locations 544 are located on one area, such as one die, and are associated with an alignment target 546. Thus, the number of alignments has dropped relatively to the situation of FIG. 5B, without reducing accuracy. One additional alignment is required for capturing reference locations 544.

Referring now to FIG. 5C together with FIG. 6, showing a flowchart of steps in a method for using local alignment targets when reviewing review locations, in accordance with some embodiments of the disclosure. In such embodiments, multiple reference locations may be captured on one dye, referred to as "reference dye", with a single alignment target. The review locations may be captured each at its intended dye. Then, each review location may be compared to the corresponding location as captured on the reference dye.

FIG. 6 depicts steps which can be performed by a system or component such as examination component 100 of FIG. 1A, after an alignment target and a review location as transformed have been captured, as described in association with FIG. 2 above. Alternatively, the steps can be performed prior to capturing the alignment target and transformed review location. Since FIG. 6 involves an additional target and an additional review location, the target, the review location and the transformed review location referred to in FIG. 2 will be referred to as "the first target", "the first review location" and "the first transformed review location".

Thus, at step 600, reference locations can be determined for two or more review locations on one reference dye. For example, a first reference transformed review location 549 for first review location 548, second reference review location 544 for second review location 547, may be determined on reference dye 542. A reference alignment target, such as reference alignment target 546 can be determined as a common alignment target for multiple reference review locations, on the same reference dye 542.

Thus, one or more reference review locations, as well as the reference alignment target may be on one reference die, which is different from the dies of the review locations.

At step 604, the wafer can be moved, and reference alignment target 546 can be captured.

At step 608, the actual location of the reference alignment target can be determined, by locating reference alignment target 546 in the captured image and determining its coordinates.

At step 612 a reference transformation can be determined, between the intended location of the reference alignment target and its actual location.

At step 616 a transformed first reference location can be determined, by applying the reference transformation to the first reference review location 549.

At step 620 the wafer can be moved and first transformed reference location can be captured.

At step 624 a second transformed reference location can be determined, by applying the reference transformation to a second reference review location 544 corresponding to a second review location 547.

For clarity, the first transformed reference location and the second a transformed reference location are not depicted in FIG. 5C separately from the first and second review locations.

At step 628 the wafer can be moved and a second transformed reference location can be captured.

At step 632, subject to differences found when comparing the image areas at the first transformed review location and at the first transformed reference location, a defect in the wafer can be reported. It will be appreciated that the same comparison can be done also for transformed second review location 547 and a second transformed reference location 544.

Thus, one additional alignment is performed, using the reference alignment target, for capturing a multiplicity of reference review locations.

However, in some cases taking reference images from dies which are far apart from each other can add noise or deformations to the reference image and make the comparison difficult and less effective. Such noise can be caused by the process variations, or by deformations caused by a long review process.

Hence comparison with closer dies may be preferred, as detailed in association with FIGS. 5D and 7 detailed below, that show a flowchart of steps in a method for using alignment targets when reviewing review locations, in accordance with some embodiments of the disclosure.

FIG. 5D depicts a situation in which for two or more review locations having one associated alignment target on the same dye or on a close dye, reference locations are determined on the same dye as the alignment target.

Thus, for review locations 588 and 589, and associated alignment target 580, reference locations 584 and 585 are added on the same die as alignment target 580. Selecting the reference locations on the same die as the alignment target adds no alignments beyond those required for the review locations. On the other hand, the reference locations are close to the review locations, thus avoiding further errors.

It will be appreciated that in some embodiments, a primary and a secondary target may be associated with each region of the wafer or with each review location, such that if, for some reason, the primary target is inappropriate, the secondary one may be used.

FIG. 7 depicts steps which can be performed by a system or component such as examination component 100, after an alignment target and a transformed first review location have been captured, as described in association with FIG. 2. Since FIG. 7 involves additional review locations, the review location and the transformed review location referred to in FIG. 2 will be denoted "the first review location" and "the first transformed review location".

At step 700, first and second reference review locations 585, 584 can be determined for first and second review locations 588, 589 associated with a common alignment target 580. Although the first and second review locations 588, 589 may be in different dies, the reference locations 584, 585 and alignment target 580 are on the same die which is close to review locations 588, 589, thus avoiding errors caused by process variations and temperature deformations.

At step 704, a first transformed reference location can be determined, for example by applying the transformation determined at step 236 of FIG. 2 to the first reference review location 585.

At step 708, the wafer can be moved and the first transformed reference location can be captured by a capture device associated with the review tool.

At step 712, a second transformed reference location can be determined, for example by applying the transformation determined at step 236 of FIG. 2 to the second reference review location 584.

For clarity, the first transformed reference location and the second transformed reference location are not depicted separately from the first and second review locations.

At step 716, the wafer can be moved and the second transformed reference location can be captured by a capture device associated with the review tool.

At step 720, subject to differences found when comparing the image areas at the first transformed review location 588 and at the first transformed reference location 584, a defect in the wafer can be reported. It will be appreciated that the same comparison can be done also for the second transformed review location 585 and at the second transformed reference location 589.

Thus, no additional alignment is performed for capturing a multiplicity of reference review locations, thus improving throughput of the system.

Thus, the situations in FIGS. 5C and 5D utilize the alignment targets for reducing the number of required alignments and thus shortening the review process, while maintaining accuracy by using local alignment targets, and in the embodiment shown in FIG. 5D also taking advantage of comparisons between nearby locations.

It will be appreciated that the methods disclosed above can be used as a single alignment method, but also in conjunction with any other alignment method, such as global alignment, dye column registration, or the like.

Figure 8:
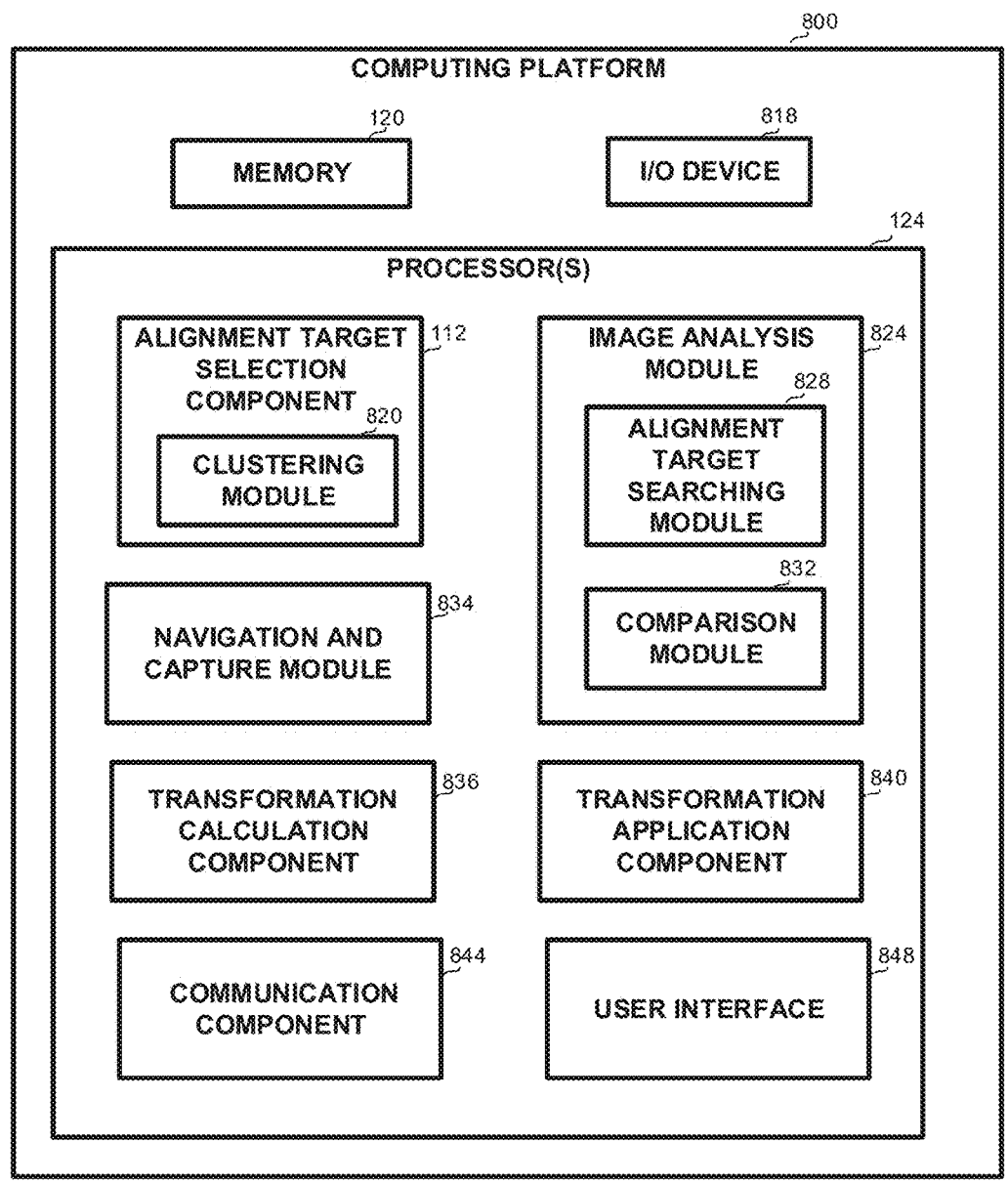
FIG. 8 shows a schematic block diagram of a system for reviewing review locations, in accordance with some exemplary embodiments of the disclosure.

Reference is now to made FIG. 8, illustrating a functional diagram of a system for examining a wafer, in accordance with some embodiments of the disclosure.

The illustrated system can comprise a computing platform 800, implementing examination component 100 and configured to execute the methods of FIG. 2, FIG. 6, and FIG. 7, and being operatively coupled to wafer movement control and capture devices. Computing platform 800 can further implement alignment target selection component 112. It will be appreciated however, that alignment target selection component 112 can be performed by another computing platform operatively coupled to computing platform 800.

Computing platform 800 can comprise a storage device 804. Storage device 804 can be a hard disk drive, a Flash disk, a Random Access Memory (RAM), a memory chip, or the like. In some exemplary embodiments, storage device 804 can retain program code operative to cause processor 812 to perform acts associated with any of the subcomponents of computing platform 800.

In some exemplary embodiments of the disclosed subject matter, computing platform 800 can comprise an Input/Output (I/O) device 808 such as a display, a pointing device, a keyboard, a touch screen, or the like. I/O device 808 can be utilized to provide output to and receive input from a user.

Computing platform 800 can comprise one or more processor(s) 812. Processor 812 can be a Central Processing Unit (CPU), a microprocessor, an electronic circuit, an Integrated Circuit (IC) or the like. Processor 812 can be utilized to perform computations required by computing platform 800 or any of its subcomponents, such as steps of the method of FIG. 2, FIG. 6 and FIG. 7.

It will be appreciated that processor 812 can be configured to execute several functional modules in accordance with computer-readable instructions implemented on a non-transitory computer-readable storage medium. Such functional modules are referred to hereinafter as comprised in the processor.

The components detailed below can be implemented as one or more sets of interrelated computer instructions, executed for example by processor 804 or by another processor. The components can be arranged as one or more executable files, dynamic libraries, static libraries, methods, functions, services, or the like, programmed in any programming language and under any computing environment.

Processor 812 can comprise alignment target selection component 112 for receiving a collection of targets, a collection of review locations to be reviewed, and an accuracy parameter and determines alignment targets.

Alignment target selection component 112 can be configured to comprise clustering module 820 which can comprise one or more clustering engines, such as K-means clustering with a kernel, mean shift clustering, or the like.

Processor 812 can be configured to comprise image analysis module 824 for analyzing images. For example, image analysis module 824 can comprise alignment target searching module 828 for locating an alignment target upon its image or one or more graphic features within an image. Image analysis module 824 can comprise comparison module 832 for comparing locations within two images and determining whether they are substantially the same. If the images are substantially the same, then it can be assumed that there is no defect in any of them. If the images are different, then at least one of them is defected, most likely the one reported as possible defect by the inspection process.

Processor 812 can be configured to comprise navigation and capture module 834 for controlling the moving of a wafer to a particular location relative to the capture device such as the SEM and initiating the capturing. It will be appreciated that moving and capturing the wafer can be controlled by another computing platform which can receive commands, send commands, or be otherwise operatively connected to computing platform 800.

Processor 812 can be configured to comprise transformation calculation component 836 for determining transformation between two points, two lines, or two two-dimensional shapes, in order to determine the deviation caused by navigation errors, spatio temporal errors, or the like.

Processor 812 can be configured to comprise transformation application component 840 for applying a transformation to a point, a line or a shape, such that the point, line, or shape undergoes the same transformation as an alignment target associated with the location.

Processor 812 can be configured to comprise reference determination component 842 for determining reference locations to review locations when required, for example when the review locations have to be compared against corresponding reference locations in another die, or the like. Reference determination component 842 can also determine reference alignment targets, located in relative corresponding locations to alignment targets, but in another area such as another die of the wafer.

Processor 812 can be configured to comprise one or more communicating components 844 for communication with other devices, such as inspection or review tools, capture devices, databases, or the like.

Processor 812 can be configured to comprise user interface 852 for receiving input from a user or providing output to a user, such as accuracy level, regions of interest, or the like. User interface 852 can exchange information with a user by utilizing I/O device 808. It is noted that the teachings of the presently disclosed subject matter are not bound by the computing platform described with reference to FIG. 8. Equivalent and/or modified functionality can be consolidated or divided in another manner and can be implemented in any appropriate combination of software with firmware and/or hardware and executed on one or more suitable devices.

The system can be a standalone entity, or integrated, fully or partly, with other entities, which can be directly connected thereto or via a network.

It is also noted that whilst the method of FIG. 2, FIG. 6 and FIG. 7 can be performed by the system of FIG. 8, this is by no means binding, and the operations can be performed by elements other than those described herein, in different combinations, or the like. It is also noted that the teachings of the presently disclosed subject matter are not bound by the flow charts illustrated in FIG. 2, FIG. 7 and FIG. 8, and the illustrated operations can occur out of the illustrated order.

It is to be understood that the disclosure is not limited in its application to the details set forth in the description contained herein or illustrated in the drawings. The disclosure is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the present disclosure may be, at least partly, implemented on a suitably programmed computer. Likewise, the disclosure contemplates a computer program being readable by a computer for executing the method of the disclosure. The disclosure further contemplates a non-transitory computer-readable memory tangibly embodying a program of instructions executable by the computer for executing the method of the disclosure.

Those skilled in the art will readily appreciate that various modifications and changes can be applied to the embodiments of the disclosure as hereinbefore described without departing from its scope, defined in and by the appended claims.

The invention claimed is:

1. A method for examining an object, the method comprising:
   receiving data indicative of a plurality of alignment targets, each alignment target being associated with a target location on an object;
   identifying a plurality of locations to be captured;
   selecting by a processor, an alignment target subset of the plurality of alignment targets, wherein each of the plurality of locations is within a determined distance from a single alignment target from the alignment target subset, the distance determined being in accordance with a provided field of view, and wherein the alignment target subset comprises fewer targets than locations to be reviewed; and
   aligning the object relative to an examination tool for capturing the locations within the determined distance from the single alignment target by using the alignment target subset.

2. The method of claim 1, further comprising:
for at least a first location of the plurality of locations:
   aligning the object such that a capture device can capture an alignment target associated with the first location;
   capturing by the examination tool a first image of the object including the alignment target;
   determining an actual location of the alignment target in the first image;
   determining a transformation between the actual location and the target location of the alignment target;
   moving the object such that the examination tool captures a transformed location obtained by applying the transformation to the first location; and
   capturing a second image of the object including the transformed location.

3. The method of claim 2, further comprising:
once the object is received for examination:
   receiving a list comprising at least one proximate location for points of interest on the object;
   determining a target having a location closest to the proximate location;
   aligning the object relative to the examination tool in accordance with the location; and
   capturing a part of the object including the point of interest.

4. The method of claim 2, further comprising:
for at least the first location, and a second location associated with a different alignment target than the first location:
   determining a first reference location and a second reference location, corresponding, respectively, to the first location and the second location, and a second alignment target common to the first reference location and the second reference location, all located in one area which is different than areas of the first location and the second location.

5. The method of claim 4, further comprising:
moving the object such that the examination tool captures the second target;
capturing a third image of the object including the second target;
determining an actual second reference target location within the third image;
determining a reference transformation between the actual reference target location and the a location of the second target;
moving the object such that the examination tool captures a first transformed reference location obtained by applying the reference transformation to the first reference location;
capturing a fourth image of a fourth part of the object including the first transformed reference location;
moving the object such that the examination tool captures a second transformed reference location obtained by applying the reference transformation to the second reference location;
capturing a fifth image of a fifth part of the object including the second transformed reference location; and
subject to detecting differences between areas of the second image associated with the first transformed location and of the fourth image associated with the first transformed reference location, indicating a defect in the object.

6. The method of claim 2, further comprising:
for at least the first location, and a second location associated with the alignment target of the first location:

determining a first reference location and a second reference location, corresponding, respectively, to the first location and the second location associated with a common alignment target, wherein the first reference location, the second reference location and the alignment target are located in one area which is different but at a maximal predetermined distance from areas of the first location and the second location.

7. The method of claim 6, further comprising:

moving the object such that the examination tool captures a first transformed reference location obtained by applying the transformation to the first reference location;

capturing a third image of a third part of the object including the first transformed reference location;

moving the object such that the examination tool captures a second transformed reference location obtained by applying the reference transformation to the second reference location;

capturing a fourth image of a fourth part of the object including the second transformed reference location; and subject to detecting differences between areas of the first image and the third image associated with the first location, indicating a defect in the object.

8. The method of claim 2, wherein the transformation is a two dimensional transformation.

9. The method of claim 2, further comprising receiving at least one review location or at least one region of interest from a human user.

10. The method of claim 1, wherein the alignment target subset is selected using clustering.

11. The method of claim 2, wherein the target location and first location are indicated in coordinates associated with design data of the object.

12. The method of claim 1, further comprising:

receiving design data of the object;

rasterizing a synthetic image of the object based on the design data; and determining the plurality of target locations by applying image processing techniques to the synthetic image.

13. The method of claim 12, further comprising:

receiving a portion of the design data for at least one potential target location; and determining an exact target location by applying processing techniques to the design data.

14. The method of claim 12, wherein the plurality of targets are determined in accordance with uniqueness in an area surrounding each target, or such that an area surrounding each target comprises a multiplicity of edges in at least two directions.

15. The method of claim 12, further comprising validating the target locations against an image of the object.

16. The method of claim 1, wherein the plurality of targets include a primary target and a secondary target for each region of the object.

17. The method of claim 1, wherein each of the plurality of locations is associated with a single alignment target.

18. The method of claim 1, wherein the examination tool is an optical inspection device or a charged particle beam based examination tool.

19. A system for examining an object, the system comprising:

a memory; and a processor, operatively coupled with the memory, to:

receive data indicative of a plurality of targets, each target associated with a target location;

identify a plurality of review locations to be captured;

select an alignment target subset of the plurality of targets, wherein each of the plurality of locations is within a determined distance from a single alignment target from the target subset, the distance determined being in accordance with a provided field of view, and wherein the alignment target subset comprises fewer targets than locations in the review locations; and align the object relative to an examination tool for capturing the locations within the determined distance from the single alignment target by using the alignment target subset.

20. A non-transitory computer readable storage medium comprising instructions, which when executed by a processor, cause the processor to perform operations comprising:

receiving data indicative of a plurality of targets, each target associated with a target location on an object;

identifying a plurality of locations to be captured;

selecting an alignment target subset of the plurality of targets, wherein each of the plurality of review locations is within a determined distance from a single alignment target from the target subset, the distance determined being in accordance with a required accuracy, and wherein the alignment target subset comprises fewer targets than locations to be reviewed; and aligning the object relative to an examination tool for capturing the locations within the determined distance from the single alignment target by using the alignment target subset.

* * * * *